United States Patent
Horiuchi et al.

(10) Patent No.: US 8,586,207 B2
(45) Date of Patent: Nov. 19, 2013

(54) FUSED POLYCYCLIC COMPOUND AND ORGANIC LIGHT EMITTING DEVICE HAVING THE COMPOUND

(75) Inventors: Takayuki Horiuchi, Tokyo (JP); Jun Kamatani, Tokyo (JP); Satoshi Igawa, Fujisawa (JP); Naoki Yamada, Inagi (JP); Masashi Hashimoto, Tokyo (JP); Tetsuya Kosuge, Kawasaki (JP)

(73) Assignee: Canon Kabushiki Kaisha, Tokyo (JP)

(*) Notice: Subject to any disclaimer, the term of this patent is extended or adjusted under 35 U.S.C. 154(b) by 482 days.

(21) Appl. No.: 12/935,627

(22) PCT Filed: May 18, 2009

(86) PCT No.: PCT/JP2009/059477
§ 371 (c)(1),
(2), (4) Date: Sep. 30, 2010

(87) PCT Pub. No.: WO2009/142314
PCT Pub. Date: Nov. 26, 2009

(65) Prior Publication Data
US 2011/0024737 A1   Feb. 3, 2011

(30) Foreign Application Priority Data

May 22, 2008 (JP) ................. 2008-134318

(51) Int. Cl.
*H01L 51/54* (2006.01)
(52) U.S. Cl.
USPC ........... 428/690; 428/917; 313/504; 313/506; 313/507; 257/40; 257/E51.05; 257/E51.026; 257/E51.032; 585/25; 585/26; 585/27

(58) Field of Classification Search
USPC .................. 428/690, 917; 313/504, 505, 506; 257/E51.05, E51.026, E51.032; 585/26, 25, 27
See application file for complete search history.

(56) References Cited

U.S. PATENT DOCUMENTS

| | | | |
|---|---|---|---|
| 6,815,090 B1 | 11/2004 | Tagami et al. | |
| 6,818,327 B2 | 11/2004 | Tagami et al. | |
| 7,709,832 B2 | 5/2010 | Negishi et al. | 257/40 |
| 7,919,197 B2 | 4/2011 | Negishi et al. | |
| 7,932,592 B2 | 4/2011 | Saitoh et al. | |
| 2003/0054200 A1 | 3/2003 | Tagami et al. | |
| 2004/0076853 A1 | 4/2004 | Jarikov | |
| 2004/0214043 A1 | 10/2004 | Tagami et al. | |
| 2006/0024523 A1 | 2/2006 | Tagami et al. | |

(Continued)

FOREIGN PATENT DOCUMENTS

| | | |
|---|---|---|
| EP | 1 762 553 A1 | 3/2007 |
| JP | 10-189247 A | 7/1998 |

(Continued)

OTHER PUBLICATIONS

Chinese Office Action issued in counterpart application No. 200980118604.3 dated Nov. 5, 2012, along with its English-language translation—13 pages.

(Continued)

*Primary Examiner* — Gregory Clark
(74) *Attorney, Agent, or Firm* — Fitzpatrick, Cella, Harper & Scinto

(57) ABSTRACT

Provided are a fused polycyclic compound obtained by expanding the conjugated system of a chrysene skeleton, and an organic light emitting device using the compound. The organic light emitting device has an optical output with high efficiency and high luminance, and is extremely durable.

7 Claims, 3 Drawing Sheets

(56) References Cited

U.S. PATENT DOCUMENTS

| | | | |
|---|---|---|---|
| 2007/0003788 A1 | 1/2007 | Tagami et al. | |
| 2008/0074045 A1 | 3/2008 | Tagami et al. | |
| 2008/0124577 A1 | 5/2008 | Saitoh et al. | |
| 2008/0224603 A1 | 9/2008 | Hashimoto et al. | 313/504 |
| 2008/0272692 A1 | 11/2008 | Hashimoto et al. | 313/504 |
| 2009/0079344 A1 | 3/2009 | Saitoh et al. | 313/504 |
| 2009/0121625 A1 | 5/2009 | Ohrui et al. | 313/504 |
| 2009/0184630 A1 | 7/2009 | Negishi et al. | |
| 2009/0278118 A1 | 11/2009 | Ohrui et al. | 257/40 |
| 2009/0278446 A1 | 11/2009 | Igawa et al. | 313/504 |
| 2009/0278447 A1 | 11/2009 | Saitoh et al. | 313/504 |
| 2009/0295279 A1 | 12/2009 | Igawa et al. | 313/504 |
| 2010/0019661 A1 | 1/2010 | Yamada et al. | 313/504 |
| 2010/0176716 A1 | 7/2010 | Igawa et al. | 313/504 |
| 2010/0237328 A1 | 9/2010 | Horiuchi et al. | 257/40 |
| 2011/0140595 A1 | 6/2011 | Negishi et al. | |

FOREIGN PATENT DOCUMENTS

| | | |
|---|---|---|
| JP | 10-189248 A | 7/1998 |
| JP | 2001-102173 A | 4/2001 |
| JP | 2003-238516 A | 8/2003 |
| JP | 2005-068087 A | 3/2005 |
| JP | 2007-306020 A | 11/2007 |
| JP | 2007-314511 A | 12/2007 |
| JP | 2008-285450 A | 11/2008 |
| WO | 01/23497 A1 | 4/2001 |
| WO | 2008/120806 A1 | 10/2008 |

OTHER PUBLICATIONS

European search report issued in corresponding application No. 09750676.0 dated Aug. 4, 2011—5 pages.

European search report issued in corresponding application No. 09750676.0 dated Aug. 14, 2012—4 pages.

Kung K. Wang et al., "Thermolysis of Benzoenyne-Allenes to Form Biradicals and Subsequent Intramolecular Trapping with a Tetraarylallene to Generate Two Triarylmethyl Radical Centers," J. Org. Chem., 1999, vol. 64, pp. 1650-1656.

FUSED POLYCYCLIC COMPOUND AND ORGANIC LIGHT EMITTING DEVICE HAVING THE COMPOUND

TECHNICAL FIELD

The present invention relates to a novel fused polycyclic compound and an organic light emitting device having the compound.

BACKGROUND ART

An organic light emitting device is a device having a thin film which contains a fluorescent or phosphorescent organic compound, and is interposed between an anode and a cathode; and injects a hole and an electron from the respective electrodes.

Then, an exciton of the fluorescent or phosphorescent compound is produced. The exciton radiates light upon return of the exciton to its ground state. The device utilizes the light.

Recent progress of an organic light emitting device is remarkable, and the characteristics of the device enable a light emitting device with a high luminance at a low applied voltage, a variety of emission wavelengths, high-speed responsiveness, thin shape, and light weight. From this fact, it is suggested that the device have potential to find use in a wide variety of applications.

However, the present situation calls for optical output with even higher luminance or higher conversion efficiency. In addition, many problems still remain to be solved regarding durability against the change over time due to long-term use, deterioration caused by atmospheric gas containing oxygen, moisture, or the like.

Further, when considering applications to a full color display and the like, the present art is still insufficient against problems relating to the need for light emission of blue, green, and red with high color purity. Therefore, a material for realizing an organic light emitting device having good color purity, high light emitting efficiency, and good durability has been demanded.

The use of a fused polycyclic compound as a component for an organic light emitting device has been proposed as a method of solving the above-mentioned problems. Japanese Patent Application Laid-Open No. 2001-102173 discloses an example in which a fused polycyclic compound is used as a component for an organic light emitting device. In addition, US Patent Application Publication No. 2004/0076853 discloses an organic light emitting device using a chrysene derivative. Japanese Patent Application Laid-Open No. 10-189248 discloses an organic light emitting device using a fluoranthene derivative. J. Org. Chem. 64, 1650-1656, 1999 discloses a fused polycyclic compound in which a chrysene skeleton and two benzene rings form a five-membered ring.

DISCLOSURE OF THE INVENTION

An object of the present invention is to provide a novel fused polycyclic compound. Another object of the present invention is to provide an organic light emitting device which has the novel fused polycyclic compound. The organic light emitting device has an optical output with high efficiency and high luminance and is durable.

The present invention provides a fused polycyclic compound represented by the following general formula (I):

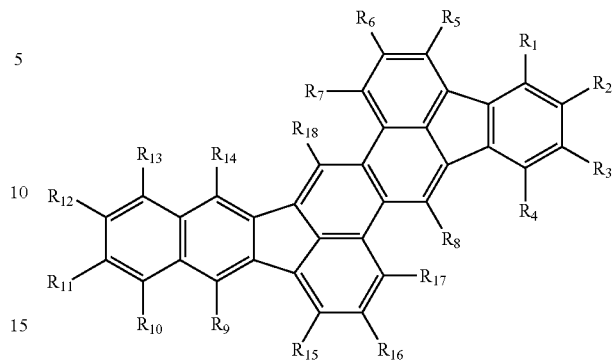

where $R_1$ to $R_{18}$ are each independently selected from the group consisting of a hydrogen atom, a halogen atom, a cyano group, a nitro group, a substituted or unsubstituted alkyl group, a substituted or unsubstituted alkoxyl group, a substituted or unsubstituted alkenyl group, a substituted or unsubstituted alkynyl group, a substituted or unsubstituted aralkyl group, a substituted or unsubstituted amino group, a substituted or unsubstituted aryl group, and a substituted or unsubstituted heterocyclic group.

The compound represented by the general formula (I) of the present invention can provide a material for an organic light emitting device having an excellent light emitting characteristic and high stability, and hence can provide an organic light emitting device which has an optical output with extremely high efficiency and extremely high luminance, and which is extremely durable.

Further features of the present invention will become apparent from the following description of exemplary embodiments with reference to the attached drawings.

DESCRIPTION OF THE EMBODIMENTS

Figure 1:
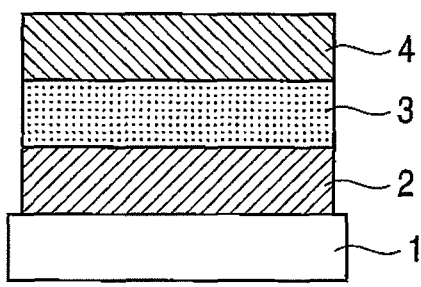
FIG. 1 is a sectional view illustrating an example of an organic light emitting device in the present invention.

A novel fused polycyclic compound according to the present invention is a fused polycyclic compound represented by the following general formula (I):

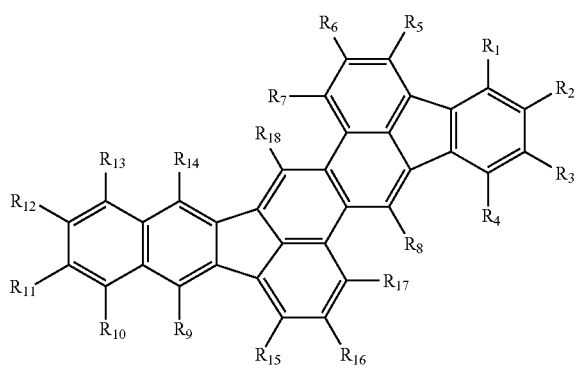

(I)

where $R_1$ to $R_{18}$ are each independently selected from the group consisting of a hydrogen atom, a halogen atom, a cyano group, a nitro group, a substituted or unsubstituted alkyl group, a substituted or unsubstituted alkoxyl group, a substituted or unsubstituted alkenyl group, a substituted or unsubstituted alkynyl group, a substituted or unsubstituted aralkyl group, a substituted or unsubstituted amino group, a substituted or unsubstituted aryl group, and a substituted or unsubstituted heterocyclic group.

Specific examples of the substituents of the fused polycyclic compound in the general formula (I) are shown below, but are not limited thereto.

Specific examples of $R_1$ to $R_{18}$ are shown below.

Examples of the halogen atom include fluorine, chlorine, bromine, and iodine.

Examples of the alkyl group include a methyl group, an ethyl group, a normal-propyl group, an isopropyl group, a normal-butyl group, a tertiary-butyl group, a secondary-butyl group, an octyl group, a 1-adamantyl group, and a 2-adamantyl group.

Examples of the alkoxyl group include a methoxyl group, an ethoxyl group, a propoxyl group, and phenoxyl group.

Examples of the alkenyl group include a vinyl group, a propenyl group, a butenyl group, a phenylvinyl group, and a diphenylvinyl group.

Examples of the alkynyl group include an ethynyl group, a propynyl group, a butynyl group, and a phenethynyl group.

Examples of the aralkyl group include a benzyl group and a phenethyl group.

Examples of the amino group include a dimethylamino group, a diethylamino group, a dibenzylamino group, a diphenylamino group, a ditolylamino group, a ditertiarybutylamino group, a dianisolylamino group, a naphthylphenylamino group, and a carbazolyl group.

Examples of the aryl group include a phenyl group, a naphthyl group, a pentalenyl group, an indenyl group, an azulenyl group, an anthryl group, a pyrenyl group, an indacenyl group, an acenaphthenyl group, a phenanthryl group, a phenalenyl group, a fluoranthenyl group, a benzofluoranthenyl group, an acephenanthryl group, an aceanthryl group, a triphenylenyl group, a chrysenyl group, a naphthacenyl group, a perylenyl group, a pentacenyl group, a biphenyl group, a terphenyl group, and a fluorenyl group.

Examples of the heterocyclic group include a thienyl group, a pyrrolyl group, a pyridyl group, a pyrimidinyl group, a bipyridyl group, an oxazolyl group, an oxadiazolyl group, a thiazolyl group, a thiadiazolyl group, a terthienyl group, a quinolyl group, a quinoxalinyl group, a carbazolyl group, an acrydinyl group, and a phenanthroryl group.

The alkyl group, the alkoxyl group, the alkenyl group, the alkynyl group, the aralkyl group, the amino group, the aryl group, and the heterocyclic group may each have a substituent. Examples of the substituent include:

alkyl groups such as a methyl group, an ethyl group, a propyl group, and a tertiarybutyl group; aralkyl groups such as a benzyl group and a phenethyl group;

aryl groups such as a phenyl group, a biphenyl group, a naphthyl group, a pyrenyl group, an anthryl group, and a fluorenyl group;

heterocyclic groups such as a thienyl group, a pyrrolyl group, a pyridyl group, a phenanthroryl group, and a carbazolyl group;

amino groups such as a dimethylamino group, a diethylamino group, a dibenzylamino group, a diphenylamino group, a ditolylamino group, and a dianisolylamino group;

alkoxyl groups such as a methoxyl group, an ethoxyl group, a propoxyl group, and a phenoxyl group;

cyano groups; nitro groups; and halogen atoms such as fluorine and chlorine.

The fused polycyclic compound represented by the general formula (I) can be mainly used as a material for an organic light emitting device.

In particular, the compound represented by the general formula (I) can be used in a hole transport layer, an electron transport layer, or an emission layer to provide a device having high light emitting efficiency and a long lifetime.

In addition, when the fused polycyclic compound represented by the general formula (I) is used in an emission layer, the compound can be used in any one of the various ways to provide a device having high color purity, high light emitting efficiency, and a long lifetime.

For example, the compound may be used alone in the emission layer. Alternatively, the compound may be used as a dopant (guest) material in the emission layer. Alternatively, the compound may be used as a host material for each of a fluorescent material and a phosphorescent material.

The content of the fused polycyclic compound represented by the general formula (I) when the compound is used as a guest is preferably 0.1 wt % or more to 30 wt % or less with respect to the total weight of the emission layer; the content is more preferably 0.1 wt % or more to 15 wt % or less in order that concentration quenching may be suppressed.

In addition, when the fused polycyclic compound represented by the general formula (I) is used as a guest, a host material is not particularly limited; a fused polycyclic derivative is preferably used in order that an organic light emitting device formed of a stable amorphous film may be provided. In addition, the host material itself is requested to have high light emitting efficiency, or the host itself is requested to have chemical stability in order that an organic light emitting device which has high efficiency and which is durable may be provided. Accordingly, a fused polycyclic derivative having high fluorescence quantum efficiency and chemical stability such as a fluorene derivative, a pyrene derivative, a fluoranthene derivative, or a benzofluoranthene derivative is more preferable.

On the other hand, when the fused polycyclic compound represented by the general formula (I) is used as a host compound, a guest is not particularly limited, and a guest has only to be appropriately used depending on, for example, a desired emission color. In addition, the compound can be used after having been doped with a hole transportable compound, electron transportable compound, or the like as well as the guest as required.

In order that the light emitting efficiency of an organic light emitting device may be improved, the emission quantum efficiency of a light emitting central material (guest) itself is desirably large. In addition, when the organic light emitting device is applied to a display device, it is important for the light emitting central material to have high color purity.

In general, at temperatures equal to or higher than room temperature, many organic compounds each show a wide fluorescence spectrum, and each tend to have poor color purity. In view of the foregoing, the following molecular design has been performed in a fused polycyclic compound: a conjugated system is expanded so that a vibrational structure may be caused to appear on the spectrum of the compound, and the color purity of the compound may be increased.

However, it is not easy to apply the above approach to blue fluorescence having large energy because the expansion of the conjugated system involves the narrowing of an energy gap.

In view of the foregoing, the inventors of the present invention have made extensive studies. As a result, the inventors have found that the fused polycyclic compound represented by the general formula (I) shows a fluorescence spectrum having a salient vibrational structure, and generates fluorescent emission having a high blue color purity. That is, a conjugated system is properly expanded by using a naphthalene ring as one of the two aromatic rings used for the formation of five-membered rings with a chrysene skeleton, and a benzene ring as the other of the two aromatic rings. With such a procedure, the relative intensity of a first peak as a 0-0 transition is made stronger than that of any other peak, and the half width of the spectrum is narrowed, whereby an increase in color purity can be achieved without the deviation of the spectrum from a blue color region.

Further, the fused polycyclic compound represented by the general formula (I) is suitable for the production of a blue organic light emitting device having high efficiency and high color purity because the compound has high quantum efficiency resulting from its rigid skeleton.

In order that an organic light emitting device which is durable may be provided, a compound for an organic light emitting device of which the device is formed must have chemical stability.

The fused polycyclic compound represented by the general formula (I) has low reactivity based on the electrophilic reaction of, for example, a singlet oxygen molecule by virtue of the electron-withdrawing effect of each of the five-membered ring structures, and is hence chemically stable. In addition, the compound, which has the two five-membered ring structures, has higher chemical stability than that of a skeleton having one five-membered ring structure such as the skeleton of fluoranthene or benzofluoranthene.

The fused polycyclic compound represented by the general formula (I) has electron-injecting property by virtue of the electron-withdrawing property of each of the five-membered ring structures. As a result, when the compound is used as a material for an organic light emitting device, the voltage at which the device is driven can be reduced. In addition, the compound, which has the two five-membered ring structures, exerts a higher reducing effect on the voltage at which the device is driven than that of a skeleton having one five-membered ring structure, such as the skeleton of fluoranthene or benzofluoranthene.

The HOMO/LUMO level of the compound represented by the general formula (I) can be easily adjusted by introducing a substituent.

Accordingly, molecular design taking a balance between the amounts in which carriers such as a hole and an electron are injected into consideration can be performed. In addition, the molecular design of light emitting materials for various emission colors can be performed.

Further, when at least one of $R_1$ to $R_{18}$ in the general formula (I) represents a substituent, the presence of the substituent leads to an avoiding effect on the overlap of the molecules of the fused polycyclic compound, and contributes to: the sublimation property and deposition stability of the compound; and the stability of a film made of the compound due to a reduction in crystallinity of the compound or the high glass transition temperature of the compound. The substituent represented by at least one of $R_1$ to $R_{18}$ is preferably a substituted or unsubstituted aryl group, or a substituted or unsubstituted heterocyclic group; $R_1$, $R_4$, $R_9$, and $R_{14}$ each more preferably represent a substituted or unsubstituted aryl group, or a substituted or unsubstituted heterocyclic group. In particular, when a substituent enters each of $R_1$, $R_4$, $R_9$, and $R_{14}$, the steric hindrance of any one of the substituents with an adjacent group is so large that the avoiding effect on the overlap of the molecules becomes large.

The present invention has been made by molecular design based on such a discussion as described above.

Hereinafter, the present invention will be described in more detail.

Specific examples of the above fused polycyclic compound represented by the general formula (I) are shown below. However, the present invention is not limited to these examples.

COMPOUND EXAMPLE 1

1-1

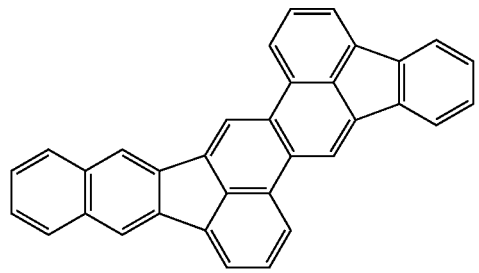

1-2

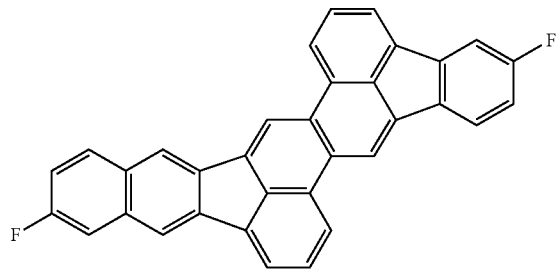

-continued
1-3
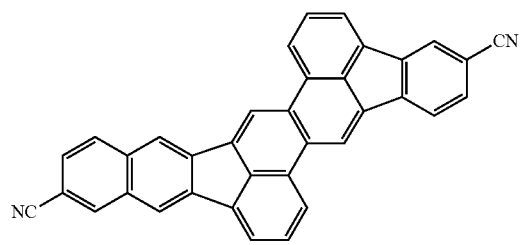
1-4
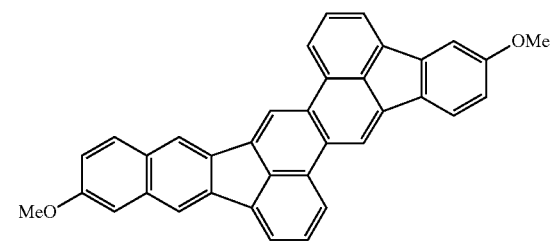
1-5
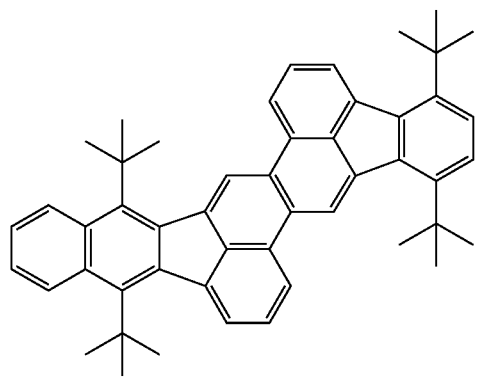
1-6
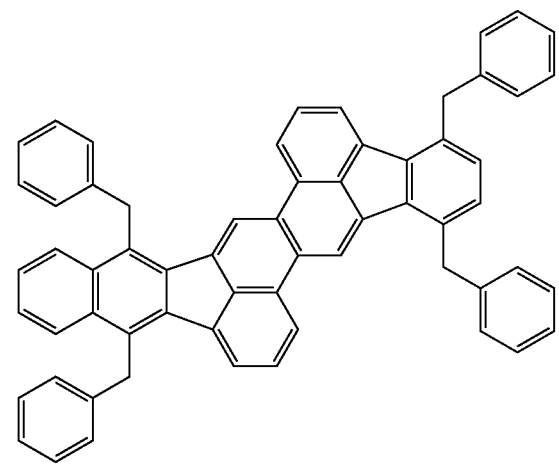
1-7
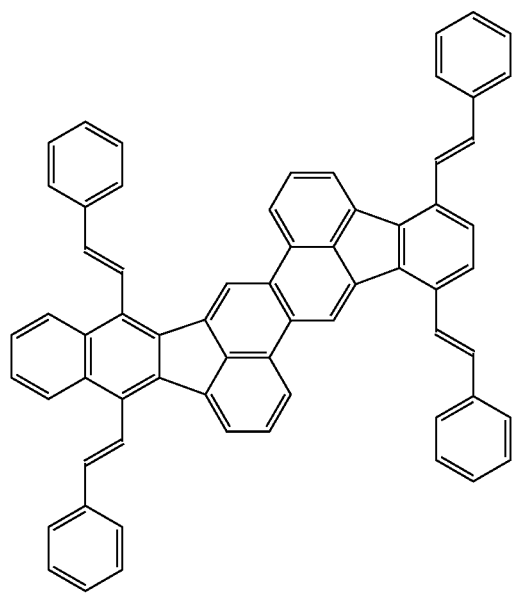
1-8
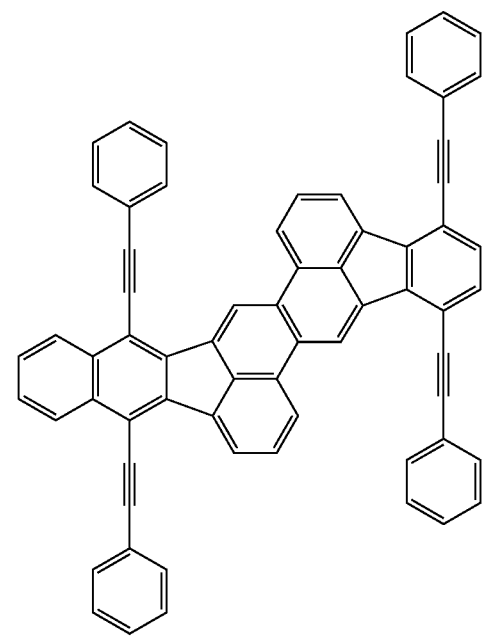
1-9
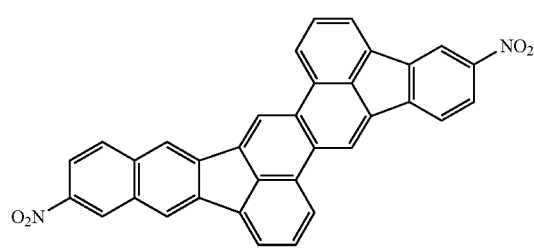

1-10
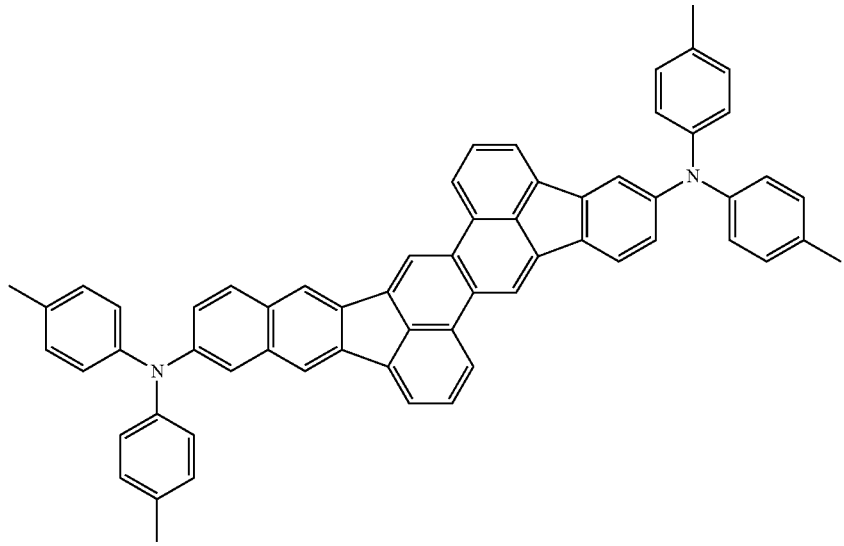
1-11
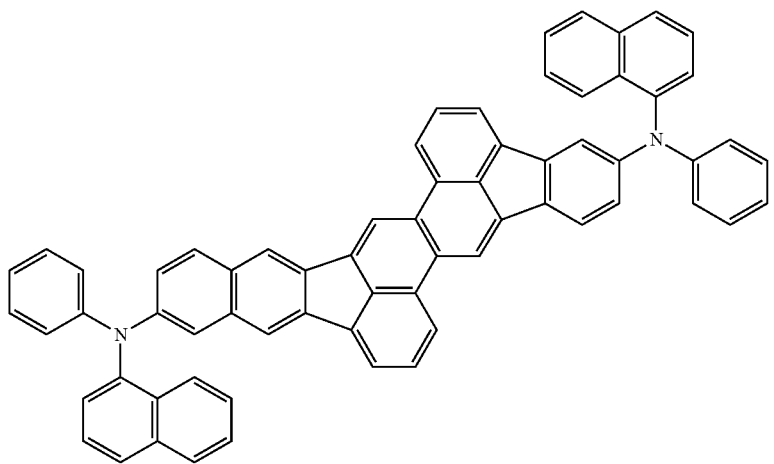
1-12
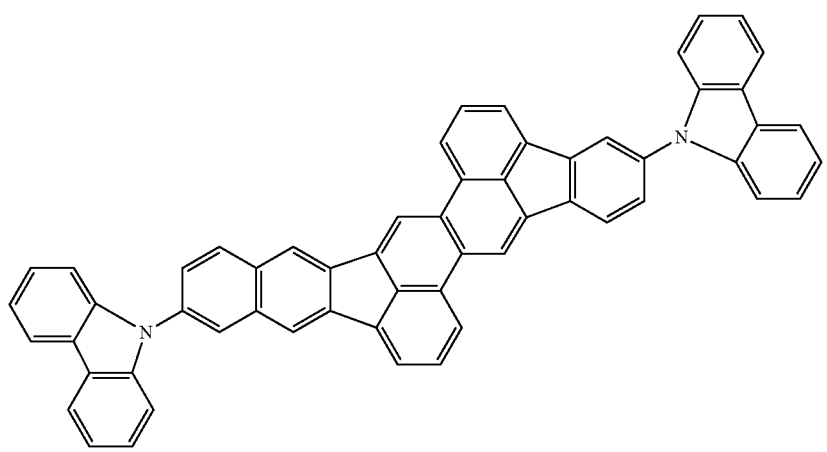

COMPOUND EXAMPLE 2
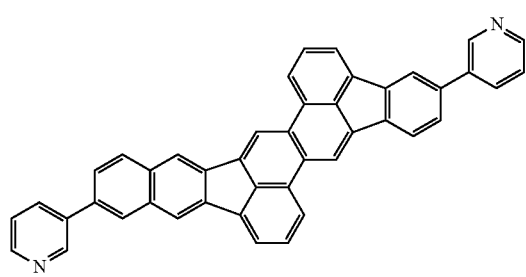
2-1
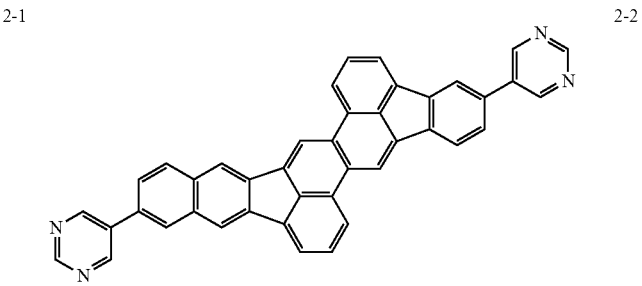
2-2
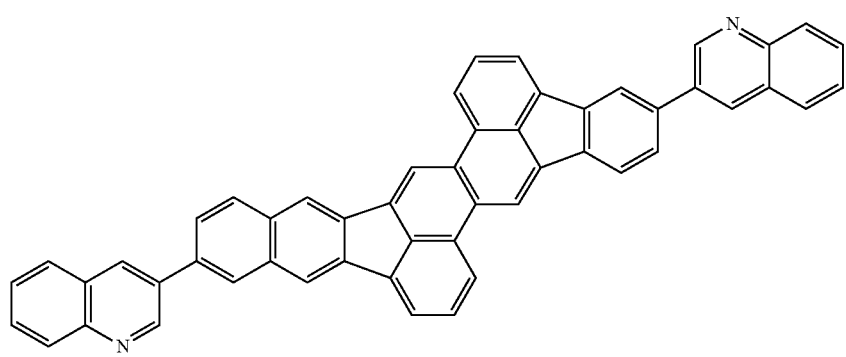
2-3
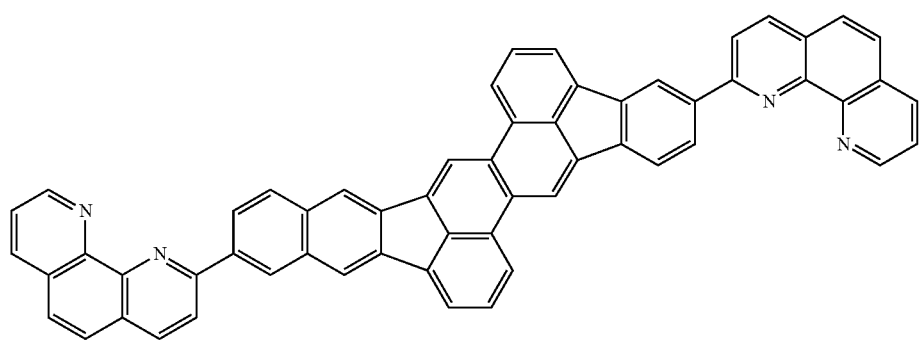
2-4
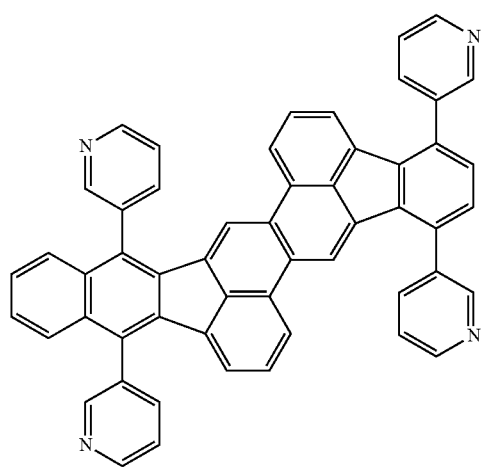
2-5
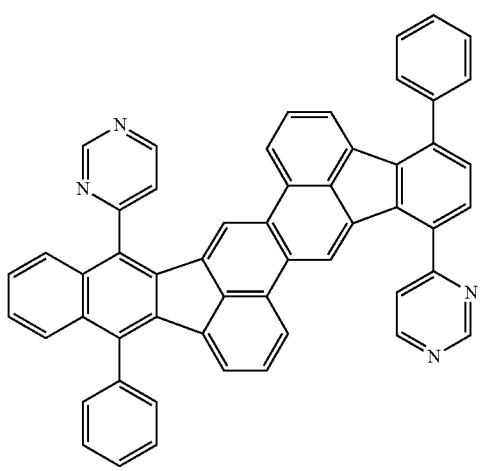
2-6

-continued
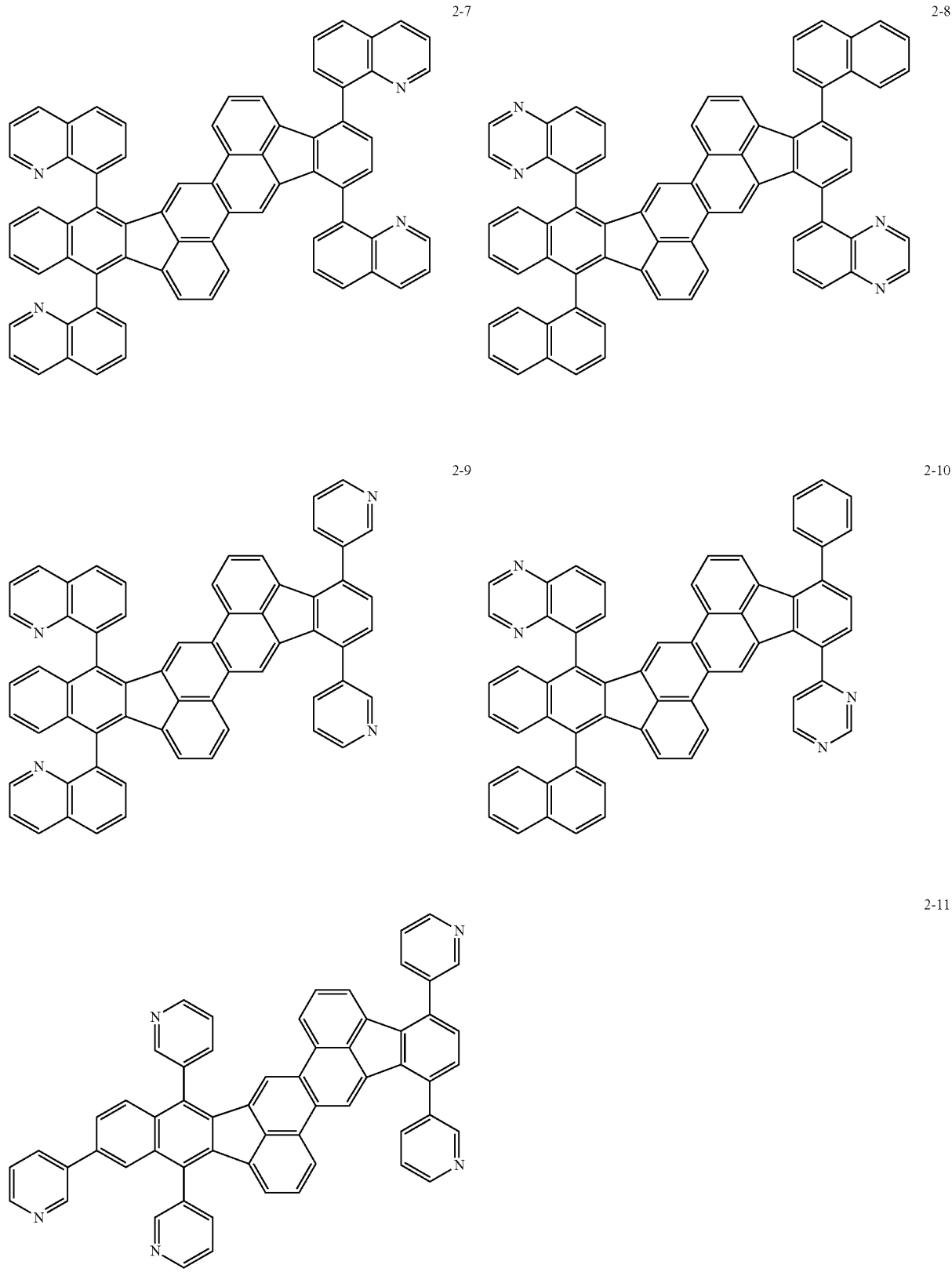

2-12
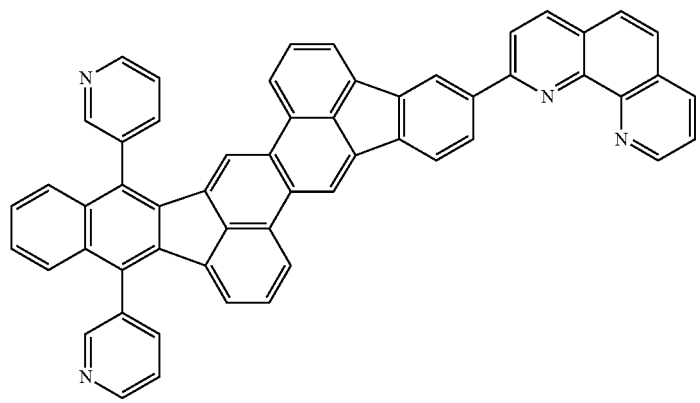
COMPOUND EXAMPLE 3
3-1
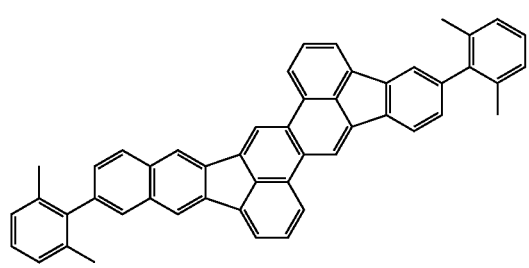
3-2
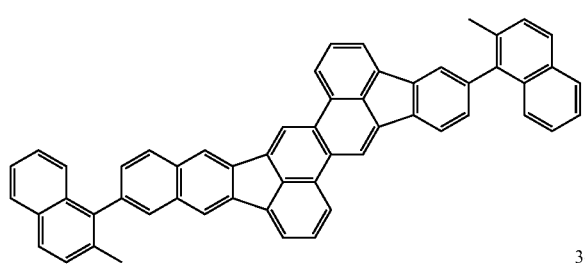
3-3
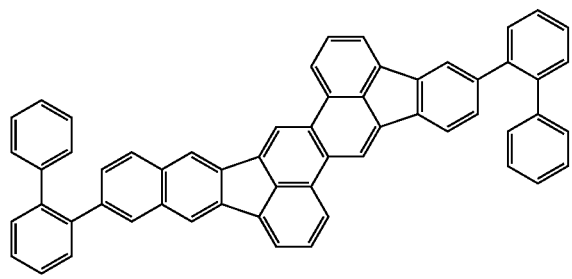
3-4
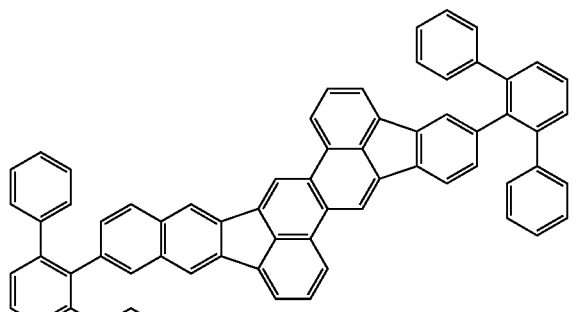
3-5
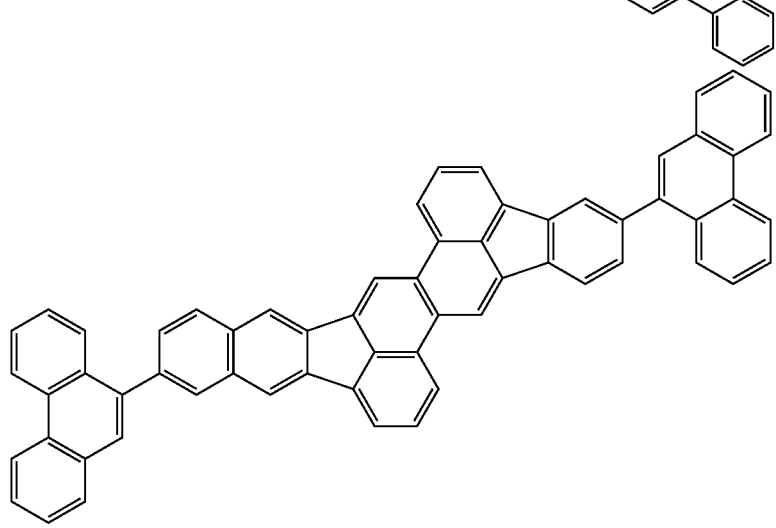

-continued
3-6
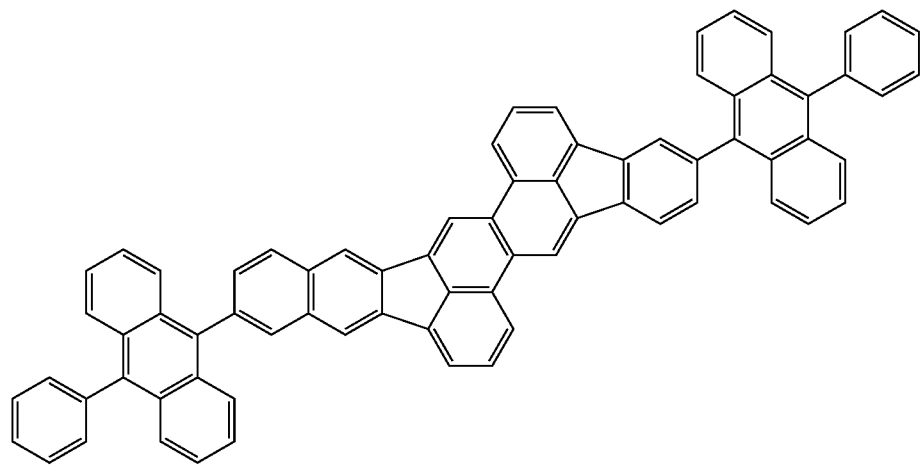
3-7
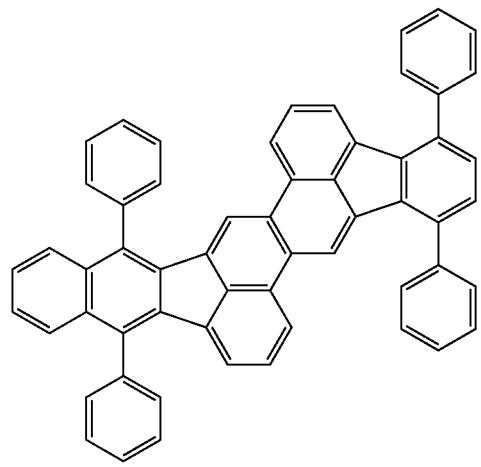
3-8
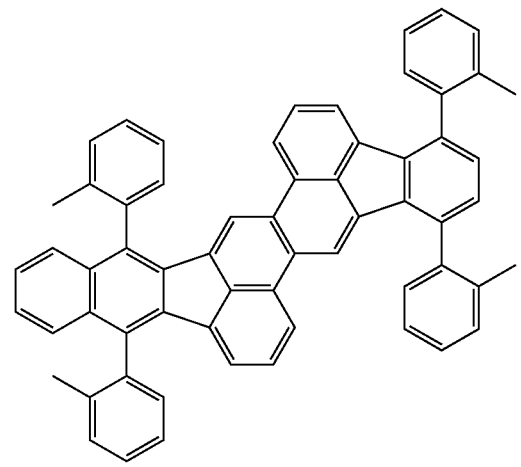
3-9
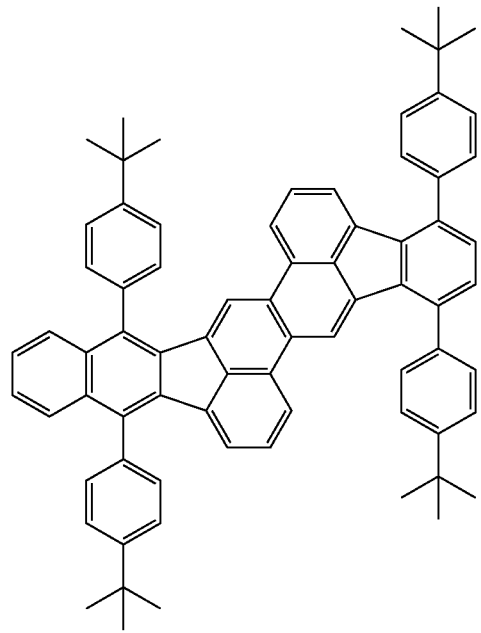
3-10
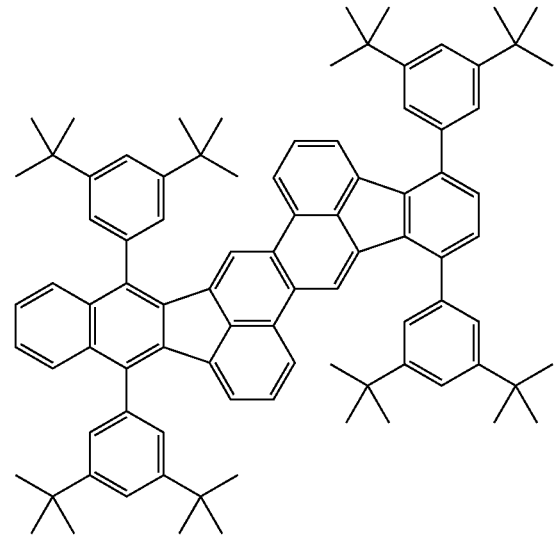

-continued
3-11
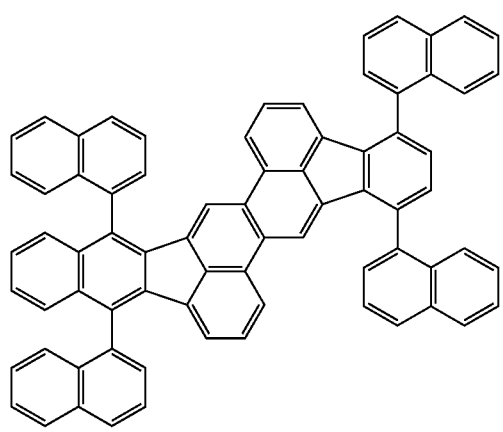
3-12
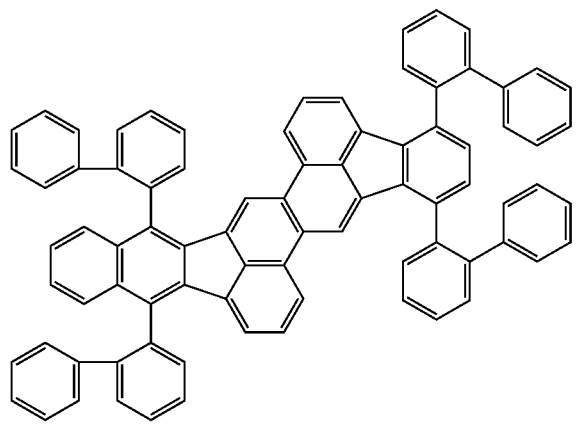
3-13
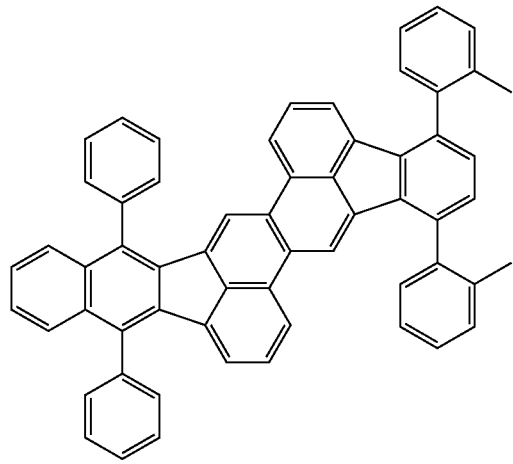
3-14
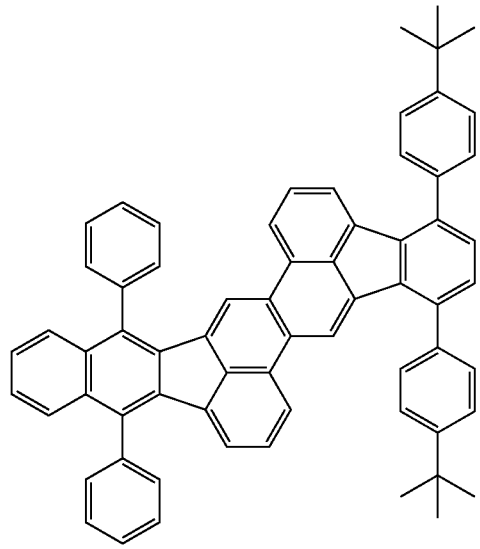
3-15
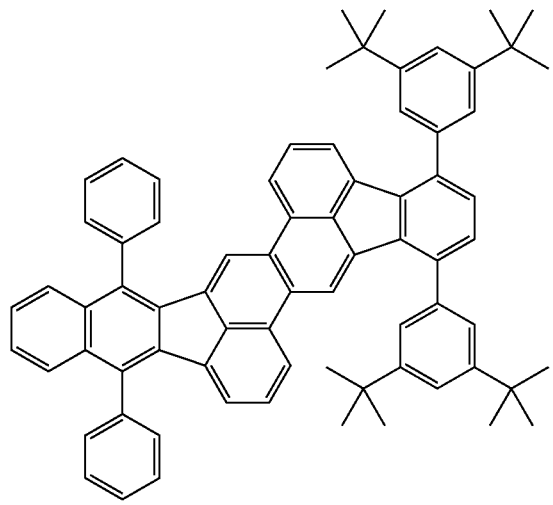
3-16
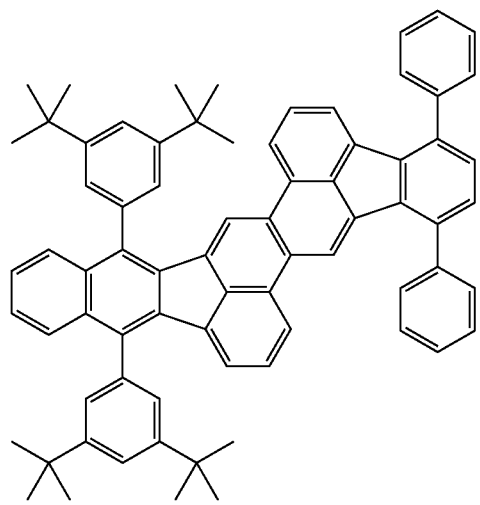

-continued
3-17
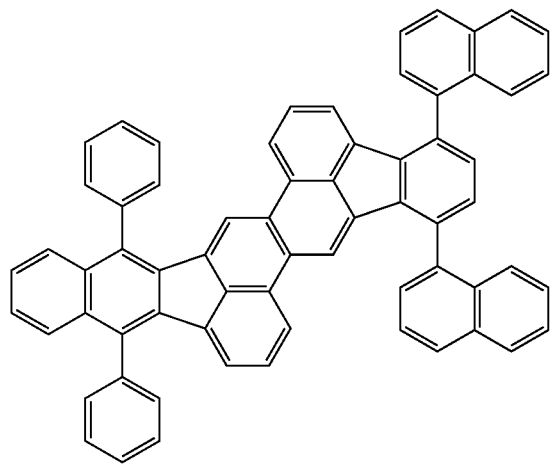
3-18
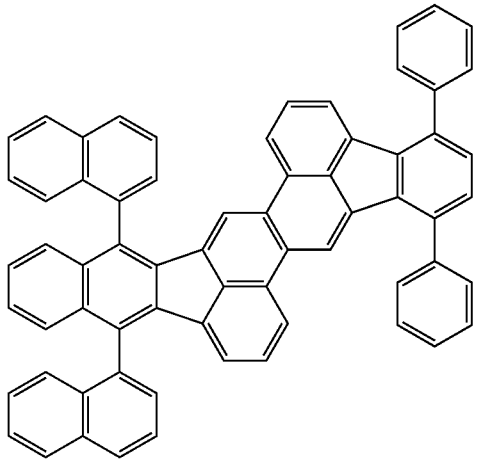
3-19
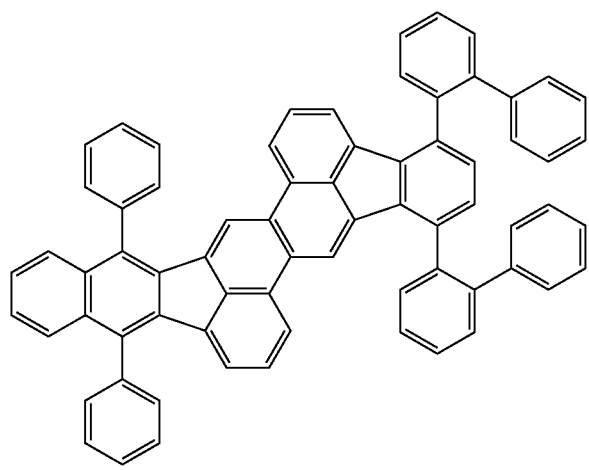
3-20
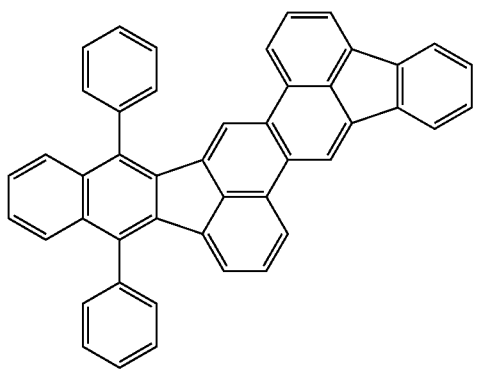
3-21
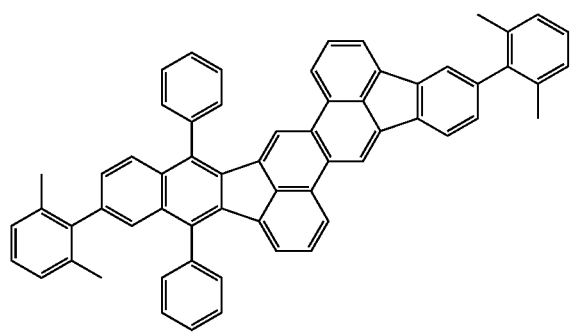
3-22
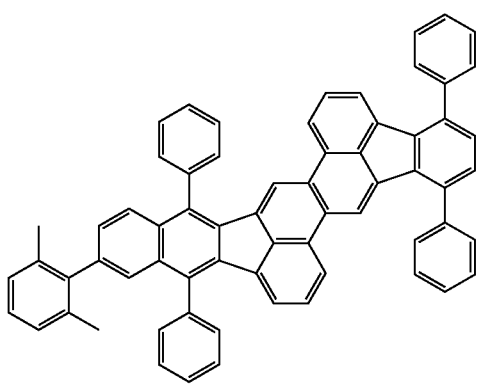

3-23
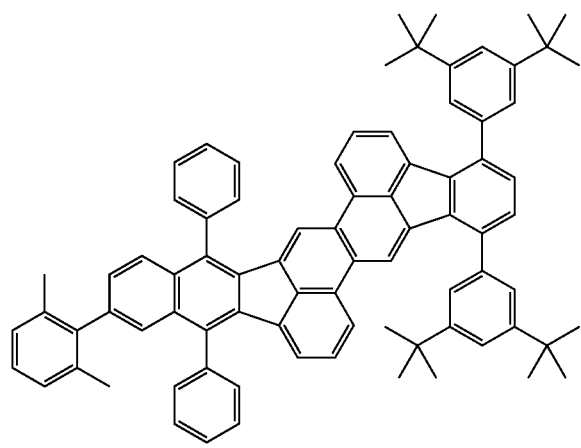
3-24
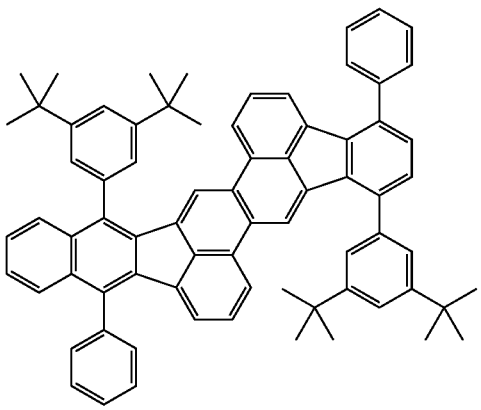
3-25
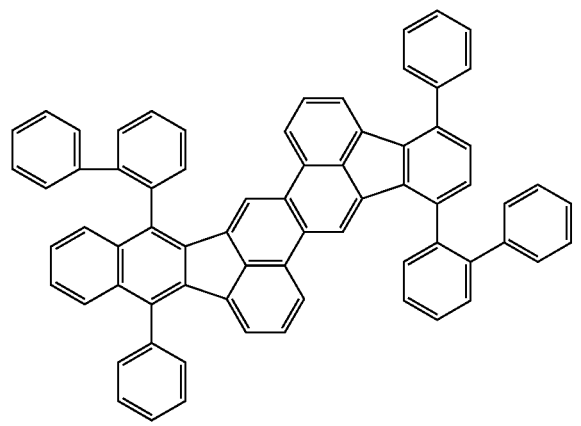
3-26
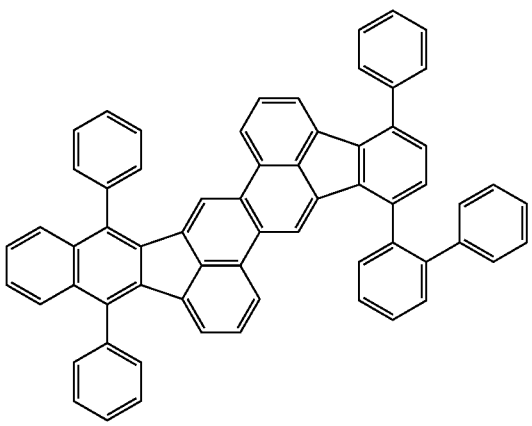
3-27
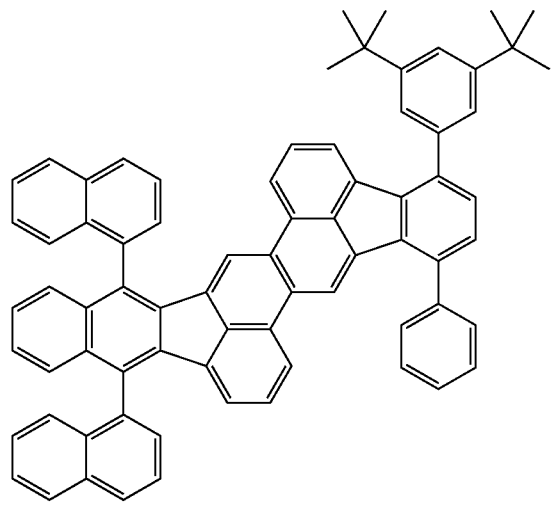
3-28
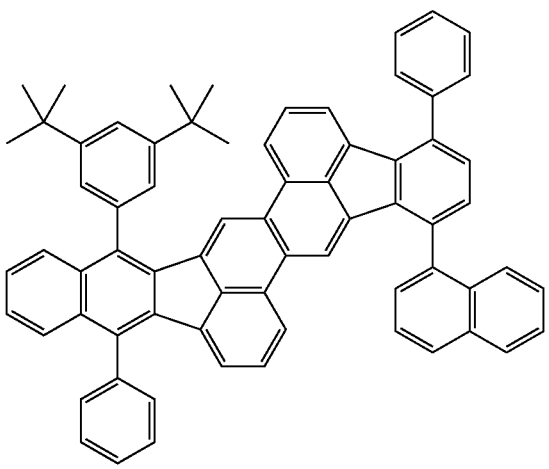

-continued 3-29
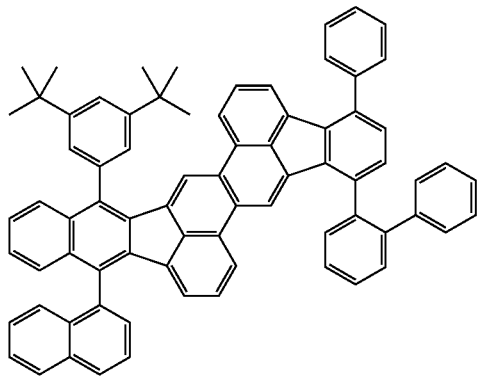

3-30
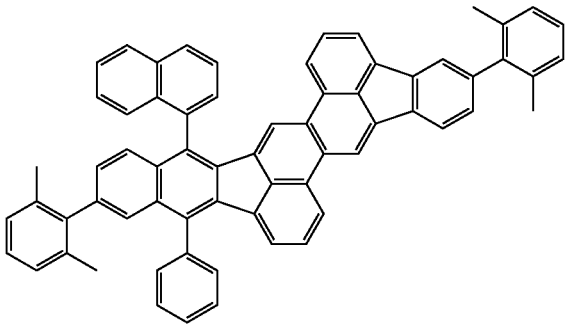

3-31
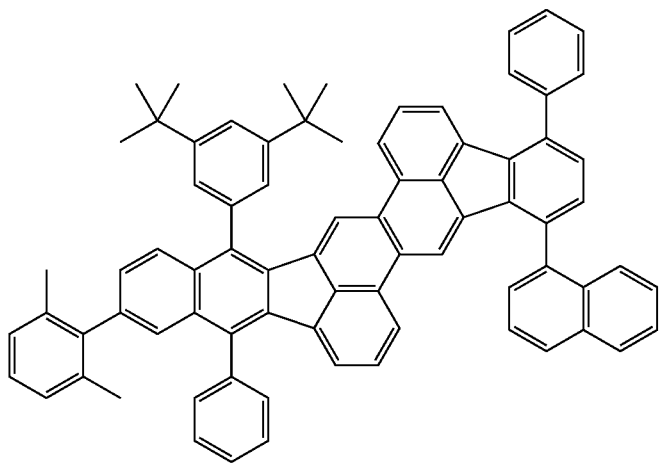

Next, an organic light emitting device of the present invention will be described in more detail.

The organic light emitting device of the present invention includes a pair of electrodes formed of an anode and a cathode, and an organic compound layer interposed between the pair of electrodes. In the organic light emitting device, the organic compound layer contains at least the fused polycyclic compound according to the present invention.

FIGS. 1 to 5 each illustrate a preferable example of the organic light emitting device of the present invention.

First, each reference numeral will be described.

Provided are a substrate 1, an anode 2, an emission layer 3, a cathode 4, a hole transport layer 5, an electron transport layer 6, a hole injection layer 7, and a hole/exciton-blocking layer 8.

FIG. 1 is a sectional view illustrating an example of an organic light emitting device according to the present invention. As illustrated in FIG. 1, the organic light emitting device has a structure in which the anode 2, the emission layer 3, and the cathode 4 are provided on the substrate 1 in the stated order. The light emitting device used herein is useful in the case where the device itself has hole-transporting property, electron-transporting property, and light emitting property or where compounds having the respective properties are used in combination.

Figure 2:
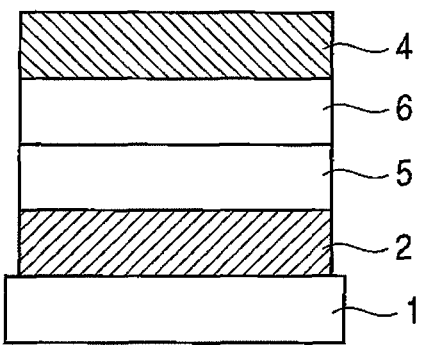
FIG. 2 is a sectional view illustrating another example of the organic light emitting device in the present invention.

FIG. 2 is a sectional view illustrating another example of the organic light emitting device according to the present invention. As illustrated in FIG. 2, the organic light emitting device has a structure in which the anode 2, the hole transport layer 5, the electron transport layer 6, and the cathode 4 are provided on the substrate 1 in the stated order. A light emitting substance is useful in the case where a material having one or both of hole-transporting property and electron-transporting property is used for each layer, and the light emitting substance is used in combination with a non-illuminant hole-transporting substance or electron-transporting substance. In this case, the emission layer 3 is formed of the hole transport layer 5 or the electron transport layer 6.

Figure 3:
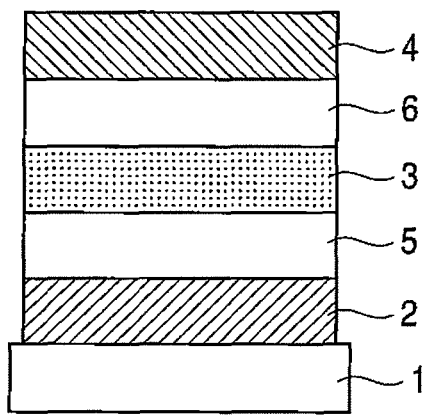
FIG. 3 is a sectional view illustrating another example of the organic light emitting device in the present invention.

FIG. 3 is a sectional view illustrating still another example of the organic light emitting device according to the present invention. As illustrated in FIG. 3, the organic light emitting device has a structure in which the anode 2, the hole transport layer 5, the emission layer 3, the electron transport layer 6, and the cathode 4 are provided on the substrate 1 in the stated order. This organic light emitting device has separate carrier-transporting function and light emitting function. The device is used in combination with compounds each having hole-transporting property, electron-transporting property, or light emitting property as appropriate, thereby allowing a substantial increase in freedom of choice in material to be used. Further, various compounds having different emission wavelengths can be used, thereby allowing an increase in the variety of emission hue. Further, light emitting efficiency may be improved by efficiently trapping each carrier or exciton in the emission layer 3 provided in the middle of the device.

Figure 4:
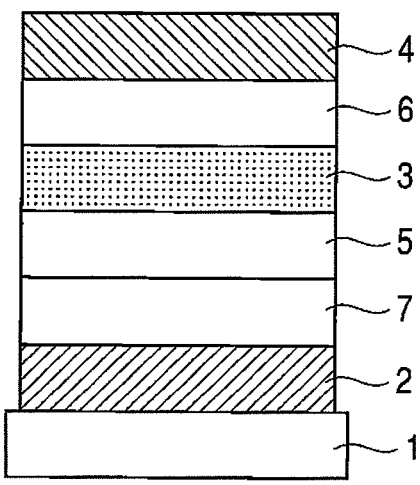
FIG. 4 is a sectional view illustrating another example of the organic light emitting device in the present invention.

FIG. 4 is a sectional view illustrating yet another example of the organic light emitting device according to the present invention. FIG. 4 has a structure illustrated in FIG. 3 except that a hole injection layer 7 is inserted into a side of the anode 2. This structure is effective for improving adhesiveness between the anode 2 and the hole transport layer 5 or for improving hole-injecting property, which is effective in lowering a voltage to be applied to the device.

Figure 5:
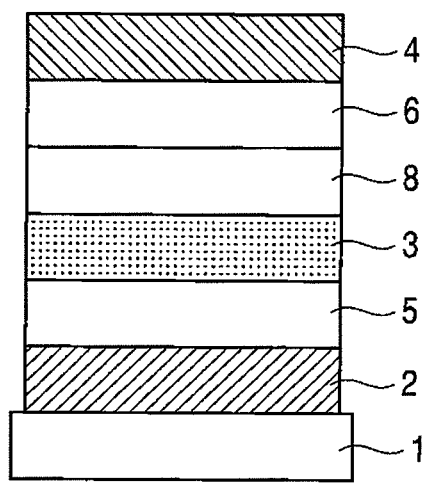
FIG. 5 is a sectional view illustrating another example of the organic light emitting device in the present invention.

FIG. 5 is a sectional view illustrating still yet another example of the organic light emitting device according to the present invention. FIG. 5 has a structure illustrated in FIG. 3 except that a layer (the hole/exciton-blocking layer 8) for blocking travel of a hole or exciton to a side of the cathode 4 is inserted between the emission layer 3 and the electron transport layer 6. This structure uses a compound having an extremely high ionization potential for the hole/exciton-blocking layer 8 and is effective for improving light emitting efficiency.

Note that FIGS. 1 to 5 each illustrate a basic device structure, and the structure of the organic light emitting device using the compound of the present invention is not limited to the structures illustrated in FIGS. 1 to 5. For example, the organic light emitting device of the present invention may have any one of the various layer structures including: a structure in which an insulating layer is provided at an interface between an electrode and an organic layer; a structure in which an adhesive or interference layer is provided; and a structure in which a hole transport layer is formed of two layers with different ionization potentials.

The fused polycyclic compound represented by the general formula (I) and used in the present invention may be used for any one of the structures illustrated in FIGS. 1 to 5.

In particular, when an organic layer using the compound of the present invention is formed by a vacuum deposition method, a solution coating method, or the like, the layer is hardly crystallized and has excellent stability over time.

In the present invention, the fused polycyclic compound represented by the general formula (I) is used particularly as a component of the emission layer. In addition, a conventionally known compound such as a low-molecular-weight-based or polymer-based hole transportable compound, luminescent compound, or electron transportable compound can be used together as required.

Examples of the hole transportable compound include: a triarylamine derivative; a phenylenediamine derivative; a triazole derivative; an oxadiazole derivative; an imidazole derivative; a pyrazoline derivative; a pyrazolone derivative; an oxazole derivative; a fluorenone derivative; a hydrazone derivative; a stilbene derivative; a phthalocyanine derivative; a porphyrin derivative; poly(vinylcarbazole); poly(silylene); poly(thiophene); and other conductive polymers.

Examples of the luminescent compound besides the fused ring aromatic compound of the present invention include: a naphthalene derivative, a phenanthrene derivative, a fluorene derivative, a pyrene derivative, a tetracene derivative, a coronene derivative, a chrysene derivative, a perylene derivative, a 9,10-diphenylanthracene derivative, rubrene, a quinacridone derivative, an acridone derivative, a coumarin derivative, a pyran derivative, Nile red, a pyrazine derivative, a benzoimidazole derivative, a benzothiazole derivative, a benzoxazole derivative, and a stilbene derivative; an organometallic complex (for example, an organic aluminum complex such as tris(8-quinolinolato)aluminum; and an organic beryllium complex), and a polymer derivative including a poly(phenylene vinylene) derivative, a poly(fluorene) derivative, a poly(phenylene) derivative, a poly(thienylene vinylene) derivative, and a poly(acetylene) derivative.

Examples of the electron transportable compound include an oxadiazole derivative, an oxazole derivative, a thiazole derivative, a thiadiazole derivative, a pyrazine derivative, a triazole derivative, a triazine derivative, a perylene derivative, a quinoline derivative, a quinoxaline derivative, a fluorenone derivative, an anthrone derivative, a phenanthroline derivative, and an organometallic complex.

Examples of a material which constitutes the anode include: a metal element such as gold, platinum, silver, copper, nickel, palladium, cobalt, selenium, vanadium, or tungsten; an alloy thereof; and a metal oxide such as tin oxide, zinc oxide, indium oxide, indium tin oxide (ITO), or indium zinc oxide. Further, a conductive polymer such as polyaniline, polypyrrole, polythiophene, or polyphenylene sulfide may also be used. Each of those electrode materials may be used alone, or two or more kinds thereof may be used in combination. Further, the anode may have a single layer structure or a multilayer structure.

Examples of a material which constitutes the cathode include: a metal element such as lithium, sodium, potassium, calcium, magnesium, aluminum, indium, ruthenium, titanium, manganese, yttrium, silver, lead, tin, or chromium; and an alloy thereof such as a lithium-indium alloy, a sodium-potassium alloy, a magnesium-silver alloy, an aluminum-lithium alloy, an aluminum-magnesium alloy, or a magnesium-indium alloy. A metal oxide such as indium tin oxide (ITO) may also be used. Each of those electrode materials may be used alone, or two or more kinds thereof may be used in combination. Further, the cathode may have a single layer structure or a multilayer structure.

The substrate to be used in the present invention is not particularly limited, but examples thereof include: an opaque substrate such as a metallic substrate or a ceramics substrate; and a transparent substrate such as a glass substrate, a quartz substrate, or a plastic sheet substrate.

In addition, the substrate may have a color filter film, a fluorescent color converting filter film, a dielectric reflection film, or the like for controlling the luminescent color. In addition, a thin film transistor (TFT) as a switching device may be produced on a substrate, and then a device which can control the on/off of light emission may be produced by connecting to the TFT. In this case, the so-called active drive is permitted. Of course, whether or not the organic light emitting device according to the present invention emits light may be controlled by the so-called passive drive (simple matrix drive).

Alternatively, the organic light emitting device according to the present invention may be driven by one of duty drive and static drive.

Regarding the emission direction of a device, the device may have a bottom emission structure (structure in which light is emitted from a substrate side) or a top emission structure (structure in which light is emitted from an opposite side of the substrate).

In addition, the following procedure may be adopted: the multiple organic light emitting devices according to the present invention are placed on the same substrate, and are each used as a pixel. In this case, a controlling unit for controlling each pixel may be further provided. In addition, in this case, a display apparatus having any such organic light emitting device as a pixel at any one of its pixel portions can be provided. The display apparatus is, for example, a thin display. Alternatively, the display apparatus may be used in the operating portion of an electrophotographic image forming apparatus.

As described above, the organic light emitting device of the present invention can be used in any one of the various apparatuses. Examples of the various apparatuses include the display and the electrophotographic image forming apparatus described above. The examples further include imaging apparatuses such as a digital still camera and a digital video camera. Alternatively, the organic light emitting device, for example, may be mounted on a display to be mounted in a vehicle such as an automobile (such as a four-wheel automobile or two-wheel automobile) or a train. Alternatively, a lighting apparatus having the organic light emitting device as its light source, or an electrophotographic image forming apparatus having the organic light emitting device as an exposure light source can be provided.

Hereinafter, the present invention is described more specifically with reference to examples, but the present invention is not limited to the examples.

EXAMPLE 1

Synthesis of Exemplified Compound 3-15

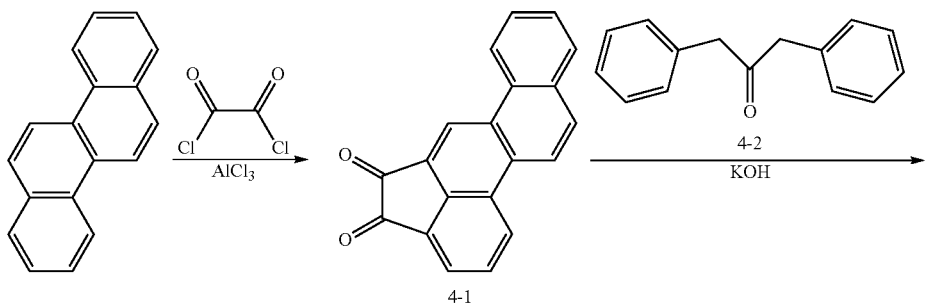

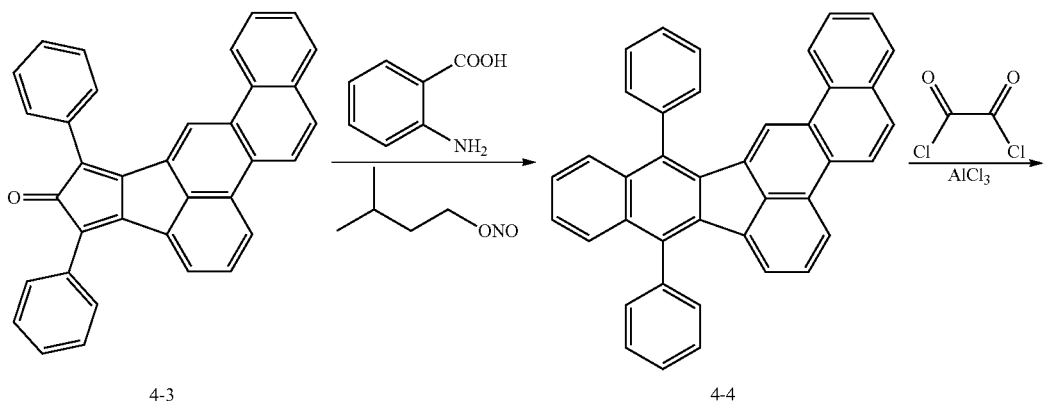

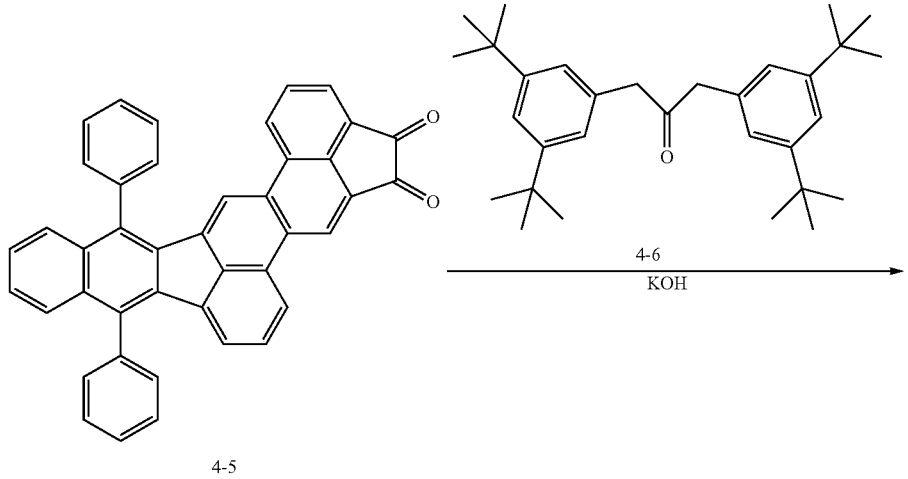

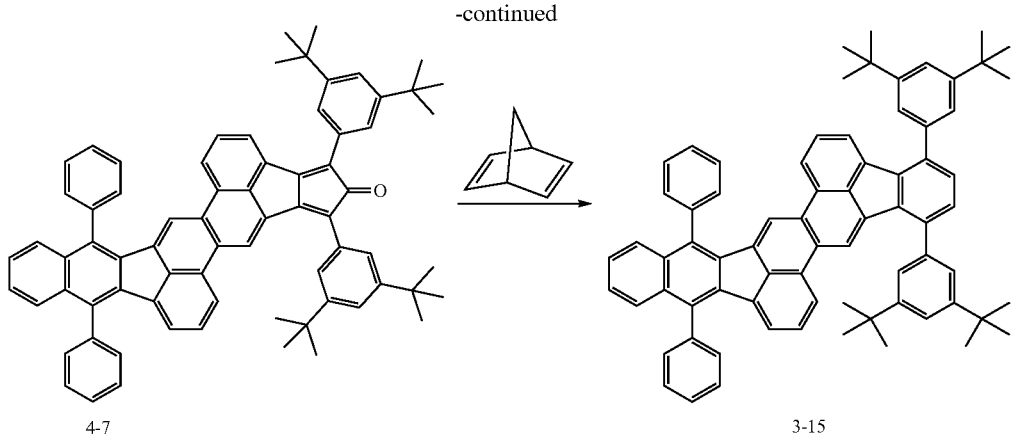

4-7 → 3-15

(a) Synthesis of Intermediate Compound 4-1

20.0 g (87.6 mmol) of chrysene, 46.7 g (350 mmol) of aluminum chloride, and 400 ml of dichloromethane were loaded into a 500-ml three-necked flask. While the mixture was stirred at −78° C. in a nitrogen atmosphere, 55.6 g (438 mmol) of oxalyl chloride were dropped to the mixture. After that, the resultant mixture was stirred for 30 minutes, and subsequently, its temperature was increased to room temperature over 2 hours. The reaction solution was poured into 4 l of ice water while the ice water was stirred. The resultant solid was separated by filtration, and was then dispersed in and washed with 100 ml of methanol. The solid was filtrated and dried by heating in a vacuum, whereby 21.5 g of Intermediate Compound 4-1 (orange powder) were obtained (87% yield).

(b) Synthesis of Intermediate Compound 4-3

2.01 g (7.10 mmol) of Compound 4-1, 1.50 g (7.13 mmol) of Compound 4-2, and 100 ml of ethanol were loaded into a 200-ml three-necked flask. While the mixture was stirred at room temperature in a nitrogen atmosphere, 25 ml of an aqueous solution in which 4.00 g of potassium hydroxide had been dissolved were dropped to the mixture. Next, the temperature of the resultant mixture was increased to 75° C., and then the mixture was stirred for 1 hour and 30 minutes. After the reaction liquid had been cooled, the precipitated solid was separated by filtration and dried, whereby 3.08 g of Intermediate Compound 4-3 (green powder) were obtained (95% yield).

(c) Synthesis of Intermediate Compound 4-4

4.00 g (8.76 mmol) of Compound 4-3, 1.26 g (9.19 mmol) of anthranilic acid, 1.50 ml (11.2 mmol) of isoamyl nitrite, and 300 ml of toluene were loaded into a 500-ml three-necked flask. In a nitrogen atmosphere, the temperature of the mixture was increased to 85° C., and then the mixture was stirred for 2 hours. After the reaction liquid had been cooled, water was added to the reaction liquid, and the mixture was subjected to two-phase extraction. The organic phase was dried with anhydrous sodium sulfate, and was then purified with a silica gel column (using a mixture of toluene and heptane as a developing solvent), whereby 2.27 g of Intermediate Compound 4-4 (yellow powder) were obtained (51% yield).

(d) Synthesis of Intermediate Compound 4-5

1.00 g (1.98 mmol) of Compound 4-4, 1.06 g (7.92 mmol) of aluminum chloride, and 50 ml of dichloromethane were loaded into a 100-ml three-necked flask. While the mixture was stirred at −78° C. in a nitrogen atmosphere, 1.26 g (9.90 mmol) of oxalyl chloride were dropped to the mixture. After that, the resultant mixture was stirred for 30 minutes, and subsequently, its temperature was increased to room temperature over 2 hours. The reaction solution was poured into 1 l of ice water while the ice water was stirred. The resultant solid was separated by filtration, and was then dispersed in and washed with 30 ml of methanol. The solid was filtrated and dried by heating in a vacuum, whereby 1.11 g of Intermediate Compound 4-5 (orange powder) were obtained (100% yield).

(e) Synthesis of Intermediate Compound 4-7

1.11 g (1.98 mmol) of Compound 4-5, 0.856 g (1.97 mmol) of Compound 4-6, 100 ml of ethanol, and 10 ml of toluene were loaded into a 200-ml three-necked flask. While the mixture was stirred at room temperature in a nitrogen atmosphere, 5 ml of an aqueous solution in which 1.11 g of potassium hydroxide had been dissolved were dropped to the mixture. Next, the temperature of the resultant mixture was increased to 75° C., and then the mixture was stirred for 1 hour and 30 minutes. After the reaction liquid had been cooled, the precipitated solid was separated by filtration and dried, whereby 0.87 g of Intermediate Compound 4-7 (green powder) were obtained (46% yield).

(f) Synthesis of Exemplified Compound 3-15

0.87 g (0.91 mmol) of Compound 4-7, 8.38 g (91 mmol) of 2,5-norbornadiene, and 40 ml of acetic anhydride were loaded into a 200-ml three-necked flask. In a nitrogen atmosphere, the temperature of the mixture was increased to 90° C., and then the mixture was stirred for 18 hours. The mixture was cooled to room temperature, and the solvent was removed by distillation under reduced pressure. After that, the remainder was purified with a silica gel column (using a mixture of toluene and heptane as a developing solvent), whereby 0.25 g of Exemplified Compound 3-15 (yellow powder) was obtained (29% yield).

Mass spectrometry confirmed that the M+ of the compound was identical to that of Exemplified Compound 3-15, i.e., 955.

Figure 6:
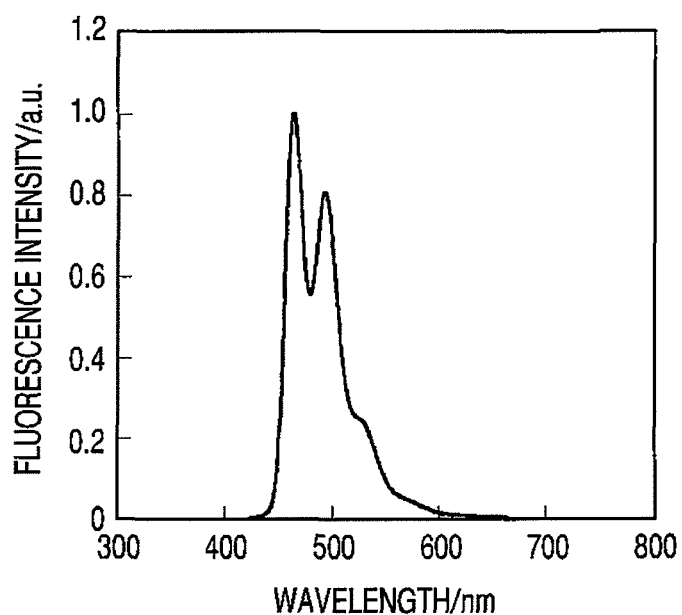
FIG. 6 is a view showing the fluorescence spectrum (excitation wavelength: 360 nm) of a solution of Exemplified Compound 3-15 in toluene ($1 \times 10^{-6}$ mol/l).

In addition, the emission spectrum of a dilute solution of the compound in toluene having a concentration of $10^{-6}$ mol/l was measured with a fluorescence spectrophotometer (F-4500 manufactured by Hitachi, Ltd.) by setting an excitation wavelength to 360 nm. As a result of the measurement, the fluorescence spectrum shown in FIG. 6 was obtained, and the compound showed good blue light emission having an emission local maximum at 464 nm.

Example 2

Synthesis of Exemplified Compound 3-7

Exemplified Compound 3-7 was synthesized by the same synthesis method as that of Example 1; specifically, the synthesis was performed under the same conditions as those of Example 1 except that Compound 4-6 in Example 1 was changed to Compound 4-2.

Mass spectrometry confirmed that the M+ of the compound was identical to that of Exemplified Compound 3-7, i.e., 730.

Figure 7:
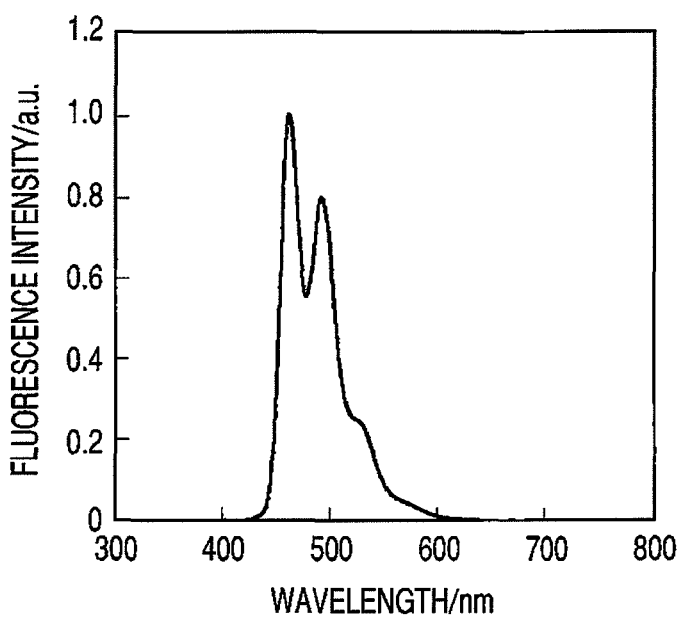
FIG. 7 is a view showing the fluorescence spectrum (excitation wavelength: 360 nm) of a solution of Exemplified Compound 3-7 in toluene ($1 \times 10^{-6}$ mol/l).

In addition, the emission spectrum of a dilute solution of the compound in toluene having a concentration of $10^6$ mol/l was measured by setting an excitation wavelength to 360 nm. As a result of the measurement, the fluorescence spectrum shown in FIG. 7 was obtained, and the compound showed good blue light emission having an emission local maximum at 463 nm.

Hereinafter, each of Exemplified Compounds 2-5, 2-9, 3-13, 3-14, 3-16, 3-17, 3-18, 3-19, 3-25, and 3-26 can be synthesized by the same synthesis method as that of Example 1; specifically, the synthesis is performed under the same conditions as those of Example 1 except that ketone derivatives shown in Table 1 below are used instead of Compound 4-2 (first ketone derivative) and Compound 4-6 (second ketone derivative) in Example 1.

| Exemplified compound | First ketone derivative | Second ketone derivative |
| --- | --- | --- |
| 2-5 | | |
| 2-9 | | |
| 3-13 | | |
| 3-14 | | |
| 3-16 | | |
| 3-17 | | |
| 3-18 | | |

-continued

| Exemplified compound | First ketone derivative | Second ketone derivative |
|---|---|---|
| 3-19 | | |
| 3-25 | | |
| 3-26 | | |

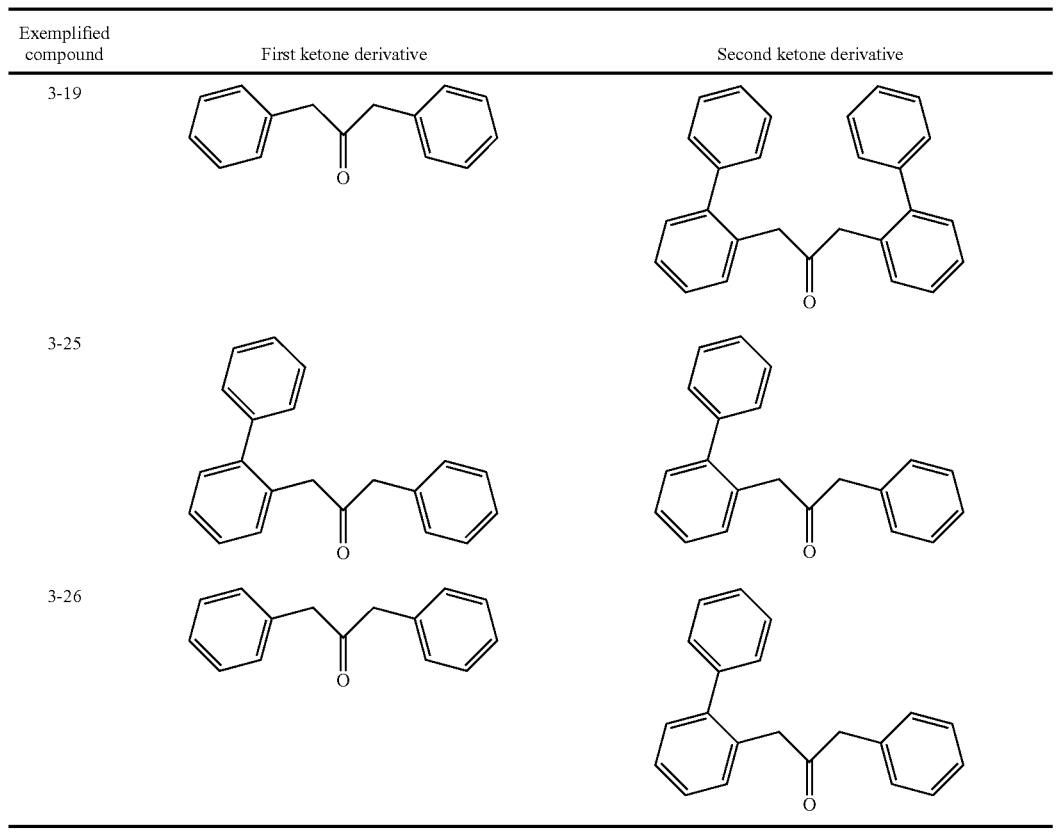

Example 3

Production of Organic Light Emitting Device

In Example 3, an organic light emitting device illustrated in FIG. 3 was produced. First, patterning was performed on a glass substrate (substrate 1) with indium tin oxide (ITO) (anode 2) having a thickness of 100 nm, to thereby produce a glass substrate with an ITO electrode. The glass substrate with an ITO electrode was subjected to ultrasonic cleaning with acetone and isopropyl alcohol (IPA) sequentially. Then, the substrate was subjected to boiling cleaning with IPA, followed by drying, and further subjected to UV/ozone cleaning. The thus treated substrate was used as a transparent conductive supporting substrate.

Next, layers each formed of an organic compound and a cathode were continuously formed on the glass substrate with an ITO electrode by vacuum vapor deposition based on resistance heating. To be specific, first, Compound A shown below was formed into a layer having a thickness of 20 nm to serve as the hole transport layer 5. Next, the emission layer 3 was formed by co-depositing Compound B shown below as a host and Exemplified Compound 3-15 as a guest so that the content of Exemplified Compound 3-15 with respect to Compound B might be 1 wt %. In this case, the thickness of the emission layer 3 was set to 30 nm. Next, Compound C shown below was formed into a layer having a thickness of 30 nm to serve as the electron transport layer 6. Next, KF was formed into a layer having a thickness of 1 nm to serve as a first metal electrode layer. Finally, Al was formed into a layer having a thickness of 100 nm to serve as a second metal electrode layer. Here, KF and Al collectively function as the cathode 4.

Compound A

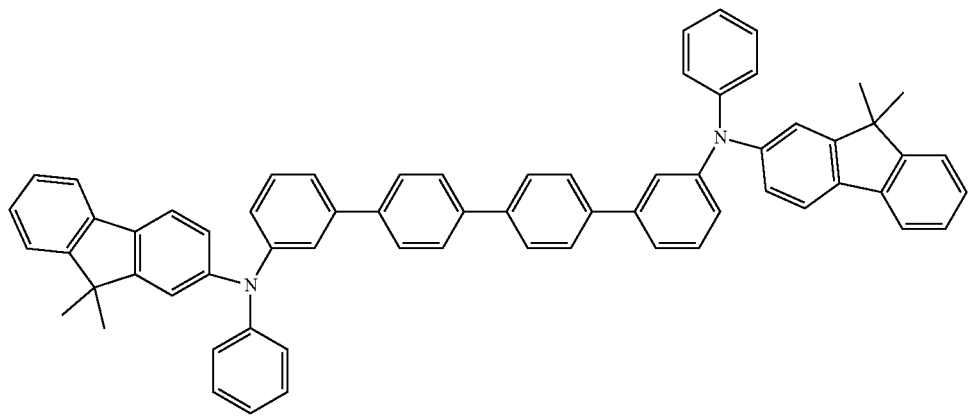

-continued

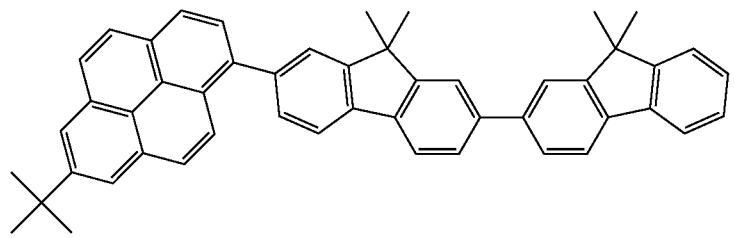

Compound B

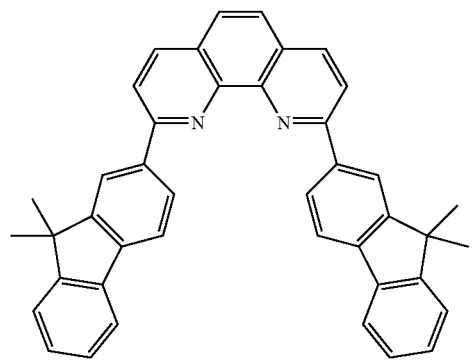

Compound C

It should be noted that the pressure in a vacuum chamber upon formation the layers was set to $10^{-5}$ Pa. In addition, opposing electrodes were each caused to have an area of 3 mm² upon production of a device. An organic light emitting device was thus obtained.

The characteristics of the resultant organic light emitting device were measured and evaluated. To be specific, the current-voltage characteristic of the device was measured with a microammeter 4140B manufactured by Hewlett-Packard Company, and the emission luminance of the device was measured with a BM7 manufactured by TOPCON CORPORATION. As a result, the device was observed to show good blue light emission having an emission luminance of 420 cd/m² at an applied voltage of 4.0 V. Further, a voltage was applied to the device under a nitrogen atmosphere for 100 hours. As a result, the device was observed to continue the good light emission.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2008-134318, filed May 22, 2008, which is hereby incorporated by reference in its entirety.

The invention claimed is:

1. A fused polycyclic compound represented by the following general formula (I):

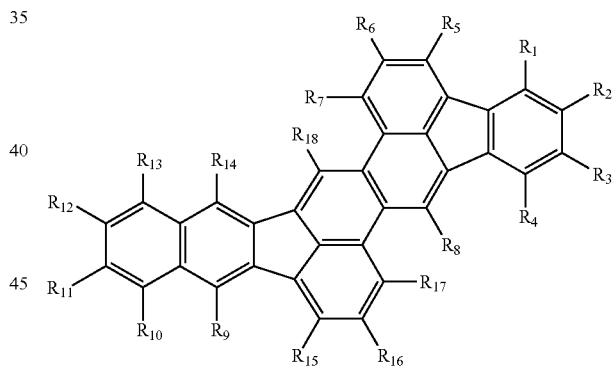

(I)

where $R_1$ to $R_{18}$ are each independently selected from the group consisting of a hydrogen atom, a halogen atom, a cyano group, a nitro group, a substituted or unsubstituted alkyl group, a substituted or unsubstituted alkoxyl group, a substituted or unsubstituted alkenyl group, a substituted or unsubstituted alkynyl group, a substituted or unsubstituted aralkyl group, a substituted or unsubstituted amino group, a substituted or unsubstituted aryl group, and a substituted or unsubstituted heterocyclic group.

2. The fused polycyclic compound according to claim 1, wherein at least one of $R_1$, $R_4$, $R_9$, and $R_{14}$ in the general formula (I) represents the substituted or unsubstituted aryl group.

3. An organic light emitting device comprising:
a pair of electrodes including an anode and a cathode; and
an organic compound layer provided between the pair of electrodes, wherein the organic compound layer contains at least the fused polycyclic compound according to claim 1.

4. The organic light emitting device according to claim 3, wherein the organic compound layer is an emission layer.

5. A display apparatus comprising:
a substrate;
a plurality of pixels; and
a control unit for controlling each of the pixels,
wherein the pixel is the organic light emitting device according to claim 3.

6. A lighting apparatus comprising a light source, wherein the light source comprises the organic light emitting device according to claim 3.

7. An electrophotographic image forming apparatus comprising an exposure light source, wherein the exposure light source comprises the organic light emitting device according to claim 3.

* * * * *